United States Patent

Bischof

Patent Number: 6,126,618
Date of Patent: Oct. 3, 2000

[54] APPARATUS FOR OBTAINING LIQUID SAMPLES

[75] Inventor: Daniel F. Bischof, McHenry, Ill.

[73] Assignee: Baxter International Inc., Deerfield, Ill.

[21] Appl. No.: 09/231,682

[22] Filed: Jan. 14, 1999

[51] Int. Cl.⁷ .............................. A61B 5/00; A61B 19/00
[52] U.S. Cl. ......................... 600/576; 604/200; 604/403; 604/409
[58] Field of Search ..................... 600/573, 575, 600/576, 577, 580, 581, 582, 584; 604/52, 53, 198, 200, 201, 205, 269, 403, 408, 409, 412, 413, 414, 415

[56] References Cited

U.S. PATENT DOCUMENTS

| | | | |
|---|---|---|---|
| Re. 35,841 | 7/1998 | Frank et al. | 604/256 |
| 2,460,641 | 2/1949 | Kleiner | 128/214 |
| 2,955,595 | 10/1960 | Semple | 128/214 |
| 3,327,709 | 6/1967 | Nehring et al. | 128/214 |
| 3,469,572 | 9/1969 | Nehring | 128/2 |
| 3,494,352 | 2/1970 | Russo et al. | 128/2 |
| 3,817,240 | 6/1974 | Ayres | 128/2 |
| 3,890,203 | 6/1975 | Mehl | 195/139 |
| 3,931,815 | 1/1976 | Takatsuki | 128/2 F |
| 4,121,585 | 10/1978 | Becker, Jr. | 128/214 R |
| 4,140,108 | 2/1979 | Nugent | 128/2 F |
| 4,212,308 | 7/1980 | Percarpio | 128/766 |
| 4,256,120 | 3/1981 | Finley | 128/764 |
| 4,295,477 | 10/1981 | Christinger | 128/766 |
| 4,296,759 | 10/1981 | Joslin et al. | 128/766 |
| 4,307,731 | 12/1981 | Kaufman | 128/766 |
| 4,320,769 | 3/1982 | Eichhorn et al. | 128/763 |
| 4,340,049 | 7/1982 | Munsch | 128/214 R |
| 4,441,951 | 4/1984 | Christinger | 156/245 |
| 4,547,186 | 10/1985 | Barlett | 604/4 |
| 4,658,655 | 4/1987 | Kanno | 73/863.85 |
| 4,759,756 | 7/1988 | Forman et al. | 604/413 |
| 4,763,648 | 8/1988 | Wyatt | 128/673 |
| 4,786,286 | 11/1988 | Cerny et al. | 604/406 |
| 4,846,795 | 7/1989 | Minagawa | 604/410 |

(List continued on next page.)

FOREIGN PATENT DOCUMENTS

| | | |
|---|---|---|
| 0175274 A2 | 3/1986 | European Pat. Off. . |
| 0084512 B1 | 1/1988 | European Pat. Off. . |
| 0414179 A1 | 2/1991 | European Pat. Off. . |
| 2 655 532 | 6/1991 | France . |
| 61 B5/14 | 2/1997 | Germany . |
| 9306976 | 11/1997 | Germany . |

OTHER PUBLICATIONS

Abstract of Spanich Utility Model Patent 1,034,664, Boletin Oficial De La Propiedad Industrial, pp. 418–419, 1977 (A partial translation of the Abstract is provided.).

*Primary Examiner*—Cary O'Connor
*Assistant Examiner*—Charles Marmor, II
*Attorney, Agent, or Firm*—Andrew G. Kolomayets; Amy L. H. Rockwell; Denise M. Serewicz

[57] ABSTRACT

An apparatus for obtaining liquid samples from a fluid flow path is disclosed. The apparatus includes a housing having an access site communicating with the flow path and carrying a piercing member at a location spaced from the access site. The housing allows for translational movement of the piercing member toward the access site and into the flow path from where the sample is removed.

20 Claims, 2 Drawing Sheets

U.S. PATENT DOCUMENTS

| | | | |
|---|---|---|---|
| 4,865,583 | 9/1989 | Tu | 604/53 |
| 4,991,601 | 2/1991 | Kasai et al. | 128/763 |
| 5,033,476 | 7/1991 | Kasai | 128/764 |
| 5,048,537 | 9/1991 | Messinger | 128/673 |
| 5,061,451 | 10/1991 | Gänshirt et al. | 422/101 |
| 5,100,376 | 3/1992 | Blake, III | 604/4 |
| 5,114,400 | 5/1992 | Lynn | 604/53 |
| 5,122,129 | 6/1992 | Olson et al. | 604/905 |
| 5,128,048 | 7/1992 | Stewart et al. | 210/749 |
| 5,167,656 | 12/1992 | Lynn | 604/409 |
| 5,201,717 | 4/1993 | Wyatt et al. | 604/192 |
| 5,270,003 | 12/1993 | Bernes et al. | 422/44 |
| 5,372,143 | 12/1994 | Bernes et al. | 128/762 |
| 5,395,347 | 3/1995 | Blecher et al. | 604/198 |
| 5,403,304 | 4/1995 | Ishida | 604/403 |
| 5,464,397 | 11/1995 | Powers, Jr. | 604/246 |
| 5,484,418 | 1/1996 | Quiachon et al. | 604/167 |
| 5,552,118 | 9/1996 | Mayer | 422/103 |
| 5,620,008 | 4/1997 | Shinar et al. | 128/764 |
| 5,649,907 | 7/1997 | Mori et al. | 604/85 |
| 5,665,074 | 9/1997 | Kelly | 604/247 |
| 5,685,875 | 11/1997 | Hlavinka et al. | 604/409 |
| 5,743,872 | 4/1998 | Kelly | 604/49 |
| 5,853,406 | 12/1998 | Masuda et al. | 604/414 |
| 5,928,166 | 7/1999 | Shemesh et al. | 600/576 |

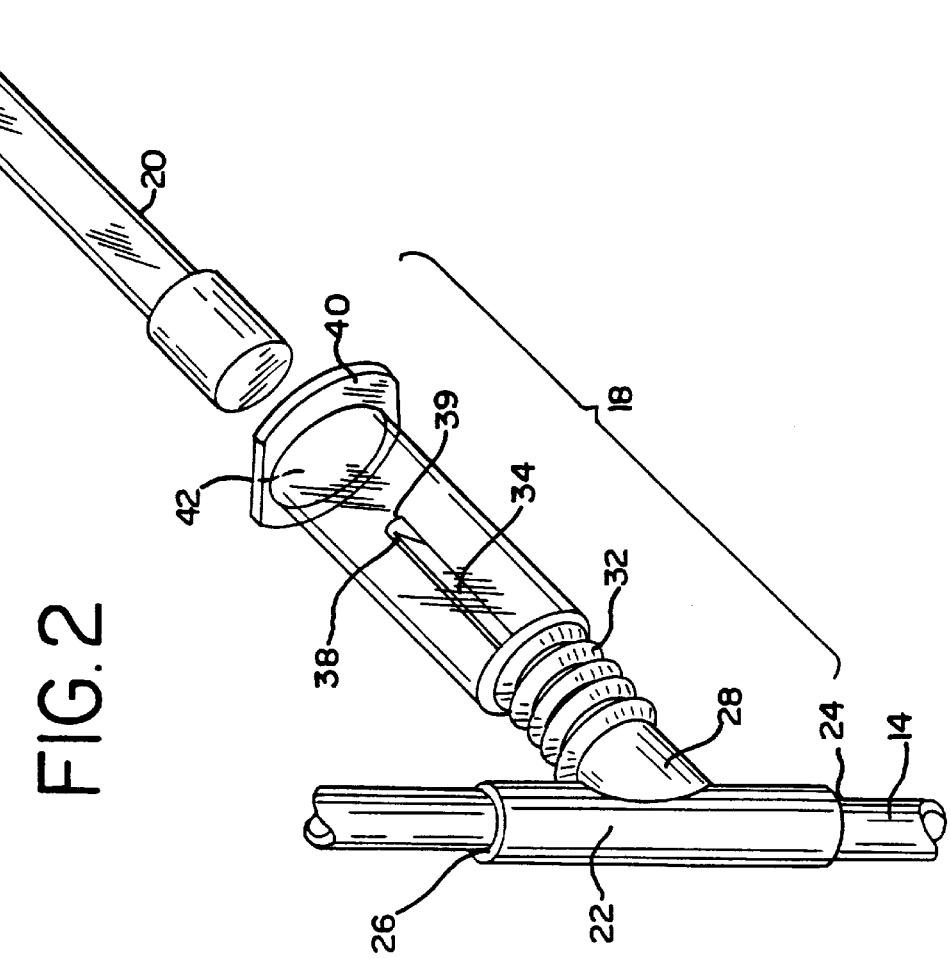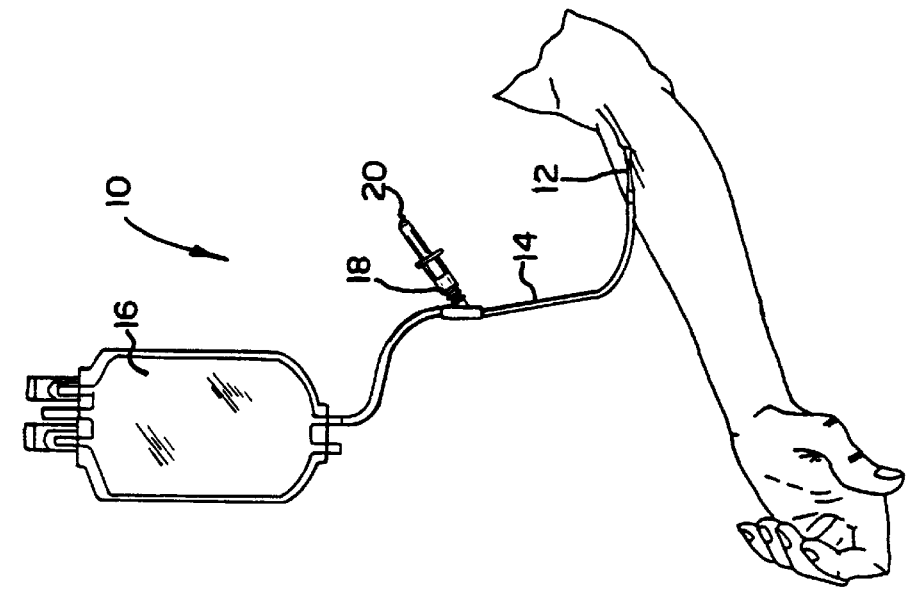

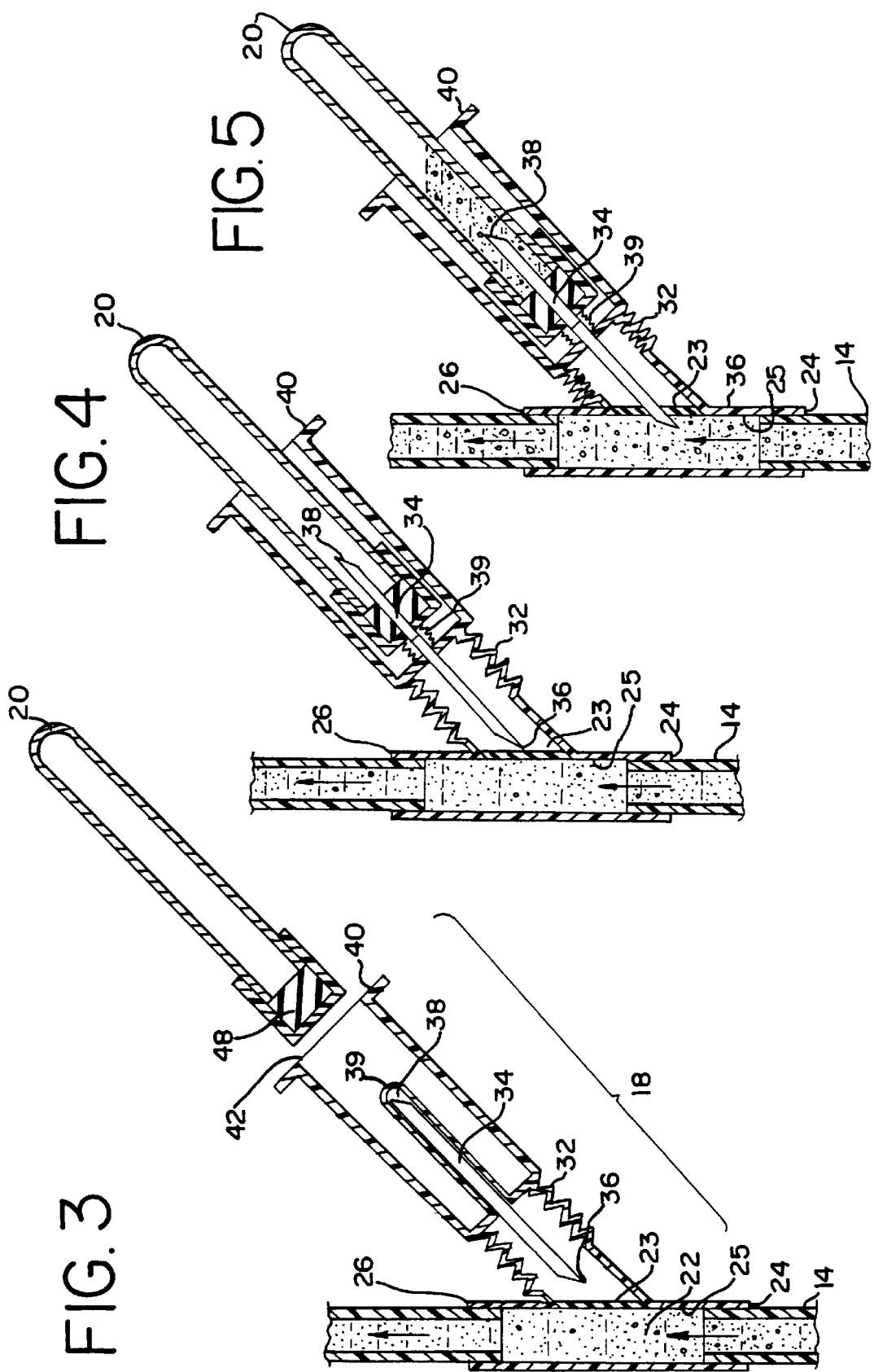

APPARATUS FOR OBTAINING LIQUID SAMPLES

BACKGROUND OF THE INVENTION

The administration of blood or blood components often plays a critical role in the emergency and/or long term treatment of patients. Blood or the individual components of blood (such as platelets, plasma, red blood cells, etc.) may be administered or transfused to patients to treat a variety of conditions. For example, blood may be administered to a patient to replace blood lost as a result of trauma, while individual blood components may be administered as part of a longer term treatment of patients suffering from cancer or certain blood related diseases. The blood or blood components administered to the patient come from blood previously collected from donors. Blood collection from donors is usually performed at a local hospital, a blood collection center or even a community center such as a local school or church as part of a blood collection drive.

One of the most common blood collection techniques, and perhaps the most well-known, is the "manual" collection of whole blood from healthy donors. As commonly understood and as used herein, "manual" collection refers to a collection method where whole blood is allowed to drain from the donor and into a collection container without the use of external pumps or similar devices. This is in contrast to the so-called "automated" procedures where blood is drawn from a donor and is pumped and, if desired, further processed by an instrument or device.

Regardless of whether the blood collection technique is manual or automated, withdrawing blood from the donor typically includes inserting a needle into the donor's arm (and, more specifically, the donor's vein) and withdrawing blood from the donor through the needle. The "venipuncture" needle typically has attached to it one end of a plastic tube that provides a flow path for the blood. The other end of the plastic tube terminates in one or more preattached plastic blood containers or bags for collecting the blood. In the manual technique, the collection container and plastic tubing may also include a volume of a liquid anticoagulant, while in the automated technique, a separate container of anticoagulant may be provided. The anticoagulant is metered into the flow path (from the anticoagulant container) where it is mixed with the incoming whole blood. In any event, anticoagulant is required because of the tendency of blood to clot and adhere to the walls of the plastic surfaces which it contacts.

After collection but prior to transfusion to a patient, the blood is typically tested for pathogens such as virus, bacteria and/or other foreign substances. Typically, testing of the collected blood requires obtaining a sample of the blood from the blood donor at or near the time of collection. One well-known technique of obtaining a blood sample is to simply withdraw or collect the blood remaining in the flow path of the disposable set after donation. This involves removing the needle from the donor, inserting the needle into a vacuum sealed sampling vial and allowing the blood from the flow path to drain into the vial. However, because there is a limited supply of blood remaining in the flow path, there may not be enough blood to provide enough of a sample to perform all of the required or desired testing. Accordingly, if a larger volume or numerous samples of blood are required, the technician obtaining the sample may continue draining the blood from the tubing, eventually withdrawing the collected anticoagulated blood from the collection container. Using blood from the container for sampling may be less desirable in that the blood has been diluted with anticoagulant. Dilution of the blood can cause errors in or at least interfere with the accuracy of certain tests. In addition, withdrawing blood from the container also reduces the volume of blood in the container.

An alternative to collecting anticoagulated blood from the collection container is to clamp off the flow path near the collection container and divert the blood being withdrawn from the donor to a collection (sampling) vial or container. This procedure typically employs a particular type of disposable tubing set having a preattached sampling site on the main flow path. Blood at or near the sampling site may be obtained by piercing the sampling site with a separately provided needle or other piercing device which may have a sampling vial attached thereto.

An example of such a sampling method and system is described in U.S. Pat. No. 5,620,008 assigned to Migada, Inc. of Englewood Cliffs, N.J. That patent describes a blood sampling unit attached to a fluid flow path and a separately provided fluid coupling device adapted to engage the sampling unit. The fluid coupling device includes a sleeve with a double-ended needle disposed within the sleeve. One end of the needle is used to pierce the sampling unit while the other end of the needle is used to pierce a sampling container or vial.

Another way of obtaining a fluid sample is described in U.S. Pat. No. 5,167,656. That patent, which is assigned to the assignee of the present application, describes a disposable tubing set wherein the flow path includes an enlarged sample collection portion. Blood for sampling is collected in the enlarged portion by clamping off the flow path near the collection container and allowing the enlarged tubing portion to fill with blood. Once the desired volume of blood for sampling is collected in the enlarged tubing portion, the needle is removed from the donor and the blood is transferred to a vial by piercing the cap of the vial with the needle and allowing the blood to drain into the sampling vial.

While the above-described methods have worked satisfactorily, further improvements in sampling sterility, safety and accuracy are desirable. For example, it would be desirable to provide a sampling system in which the needle used to withdraw blood from the flow path is never exposed to the outside environment and is, therefore, less susceptible to contamination by the outside environment or accidental needle puncture of the user. It would also be desirable to provide a sampling system wherein the possibility of collecting any residual anticoagulant that may be present at or near the site (which could result in dilutional errors) is substantially eliminated. Thus, it would be desirable to provide a sampling system in which (1) the needle or piercing member can be advanced into the flow path of the blood and/or (2) "dead spaces" where anticoagulant can accumulate or insufficiently anticoagulated blood components collect and clot are substantially avoided. It would also be desirable to provide a sampling system in which transfer of blood does not require removal of the venipuncture needle and reinsertion of the needle (into the vial), but instead permits the blood to flow directly from the donor to the sampling vial. It would also be desirable to provide a sampling system which is integrated with the blood collection set and requires few separate or external components.

SUMMARY OF THE INVENTION

One or more of the foregoing benefits is achieved by the present invention which, in general, is directed to an apparatus for obtaining a liquid sample from a fluid flow path. In accordance with one aspect of the present invention, the apparatus may include a housing that has an inlet, an outlet and a flow path between the inlet and outlet. The housing may comprise an access site that communicates with the flow path between the inlet and outlet. The housing may carry a piercing member at a location spaced from the access site and allow for translational movement of the piercing member toward the access site to pierce the access site and enter the flow path.

In accordance with another aspect of the present invention, the housing may allow for translational movement of the piercing member by including a length adjustable sleeve proximally attached to the access site. The length adjustable sleeve may be flexible and compressible.

In accordance with another aspect of the present invention, the housing may further include a receptacle with an interior adapted for receiving a liquid sample container. Where a length adjustable sleeve is used to allow for translational movement of the piercing member, the receptacle may be proximally attached to the sleeve.

In accordance with another aspect of the present invention, the piercing member may include first and second opposed piercing ends. For example, where the housing includes a length adjustable sleeve and a receptacle, one end of the piercing member may be disposed within the length adjustable sleeve. The other opposed end of the piercing member may be disposed within the interior of the receptacle.

The present invention is also directed to a disposable tubing set for processing biological fluid such as blood. In accordance with one aspect of the present invention, the disposable tubing set may include means for withdrawing blood from a blood source and a container for receiving the blood. The disposable tubing set may also include a flow path between the withdrawing means and the container, the flow path including a housing having an inlet, an outlet and an access site communicating with the flow path between the inlet and outlet. In accordance with one aspect of the present invention, the housing may carry a piercing member at a location spaced from the access site and allow for translational movement of the piercing member toward the access site. In accordance with another aspect of the present invention, the means for withdrawing the whole blood may include a venipuncture needle for insertion into a human donor.

BRIEF DESCRIPTION OF THE DRAWINGS

FIG. 1 is a perspective view of a disposable blood collection set embodying the present invention.

FIG. 2 is a perspective view of an apparatus for obtaining a liquid sample from the fluid flow path embodying the present invention.

FIG. 3 is a side cross-sectional view of the apparatus of FIG. 2 with a liquid sample container outside the receptacle.

FIG. 4 is a side cross-sectional view of the apparatus of FIG. 2 with a liquid sample container disposed within a receptacle and a piercing member at a location spaced from the access site.

FIG. 5 is a side cross-sectional view of the apparatus of FIG. 2 with the piercing member advanced into the flow path of the liquid.

DETAILED DESCRIPTION OF THE DRAWINGS

Turning now to FIG. 1 of the drawings, the present invention may be embodied in a liquid flow conduit or set such as a disposable tubing set 10, which is particularly suitable for use in the manual collection of blood from a donor. The illustrated disposable set 10 may include a needle such as venipuncture needle 12, and a length of plastic tubing 14 extending from needle 12 to a collection container such as a flexible plastic bag 16. In accordance with the present invention, disposable tubing set 10 includes housing 18, for providing access to blood flowing therethrough. As shown in FIGS. 1 and 2, the disposable tubing set 10 and more specifically, housing 18, is adapted to receive a sampling vial 20 into which the blood is collected.

As shown in FIGS. 2 and 3 (in cross-section), housing 18 defines a flow path 22 having flow inlet 24, flow outlet 26 and an access site 23 communicating with flow path 22 (FIG. 3). Housing 18 may be of any desired shape, but preferably includes the primary flow path 22 and a leg 28 branched from flow path 22. For example, as shown in the illustrated embodiment, housing 18 has a Y-type configuration with leg 28 branched from flow path 22.

Housing may be made of any suitable, biocompatible and sterilizable material. Most typically, housing 18 may be made of a flexible plastic material capable of being bonded, such as by solvent bonding, to the plastic tubing portion 14 of disposable tubing set 10. As shown, for example in FIGS. 3–5, flow inlet 24 of housing 18 is bonded to tubing portion 14 that extends from venipuncture needle 12. Similarly, flow outlet 26 may be bonded to tubing portion 14 that extends to collection container 16.

As further shown in FIGS. 2 and 3, housing 18 carries piercing member 34. More specifically, housing 18 carries piercing member 34 at a location proximally spaced from access site 23. In accordance with the present invention, housing 18 allows for translational movement of piercing member 34 toward access site 23. Piercing member 34 includes a first piercing end 36 and a second piercing end 38.

Referring back to FIG. 3, the interior of housing 18 includes access site 23. Access site 23 separates and seals flow path 22 from the remainder of the housing, including piercing member 34. In a preferred embodiment, access site 23 is located as near as possible to flow path 22, thereby avoiding "dead spaces" where, for example, anticoagulant may reside and/or blood components may coagulate. For example, as shown in FIGS. 3–5, access site is substantially co-planar with the wall 25 of housing 18, which wall defines, in part, flow path 22. Although any type of piercable member that allows access to flow path 22 may be employed without departing from the present invention, in one preferred embodiment, access site 23 is a piercable septum which may be made of latex, silicone, plastic or any other material that may be sterilizable and is piercable by piercing member 34. It may be desirable that septum be made of a material that is repeatedly piercable by piercing member 34. It is also desirable that the septum be substantially resealable after piercing.

As set forth above, housing 18 allows for translational movement of piercing member 34 toward access site 23. In one embodiment of the present invention, housing 18 includes a length adjustable sleeve 32 to allow for the translational movement of piercing member 34. In a preferred embodiment, the length adjustable sleeve is a compressible sleeve such as shown in FIGS. 2 through 5. The compressible length adjustable sleeve 32 may be made of a flexible deformable, resilient plastic or rubber material that is substantially hollow inside so as to receive piercing member 34. Of course, it will be understood that length adjustable sleeve 32 may have any structure or be made of any material which allows the length of the sleeve to be adjusted and/or allows for translational movement of piercing member 34. For example, length adjustable sleeve 32 may include two or more telescoping sleeves which would also allow for advancement or translational movement of piercing member 34 toward access site 23.

Housing 18 may also include receptacle 40. As shown in FIGS. 2 and 3, receptacle 40 may be proximally located from access site 23. Receptacle 40 may be in the form of a hollow cylinder open at its proximal end and defining an interior chamber 42 for receiving sampling vial 20. In the embodiments where housing includes a length adjustable sleeve, receptacle 40 may be proximally attached to such sleeve at the distal end of receptacle 40 as shown in FIGS. 2 through 5. In fact, in order to reduce the number of external components required for obtaining a liquid sample, it is preferred that housing 18 include the sleeve 32, piercing member 34 and receptacle 40 as a pre-assembled or otherwise integral unit. Alternatively, but perhaps less preferably, receptacle 40 may be a separately provided component with or without piercing member 34. In any event, receptacle 40 may be made of any plastic sterilizable material having an interior that is adapted to receive sampling vial 20 and that can be held in the palm of the hand of the technician or person obtaining the sample. Receptacles of the type generally discussed above are described in U.S. Pat. No. 4,991,601, (which is incorporated by reference herein) and are available from, for example, Terumo Kabushiki Kaisha of Tokyo, Japan.

Piercing member 34 may be a needle, cannula or other biocompatible device having a sharpened tip. As set forth above, piercing member 34 includes a first piercing end 36 and an oppositely directed second piercing end 38. Piercing member 34 may be carried on the housing and integral with length adjustable member 32 and/or receptacle 40. In a preferred embodiment where housing 18 includes a length adjustable sleeve 32 and receptacle 40 proximally attached thereto, the first piercing end 36 is located within sleeve 32 and the second piercing end 38 is located within receptacle 40. Piercing member 34 may be made of any material of sufficient strength such as metal or plastic. In addition, end 38 of piercing member 34 may be enclosed within a protective sheath 39. Protective sheath 39 may preferably be made of a flexible material, such as latex, which is capable of being penetrated by the tip of piercing member end 38. Also protective sheath 39 should be sufficiently resilient to return to its original shape (covering end 38) upon withdrawal of sampling vial 20 (as described below).

In accordance with the method of collecting a blood sample from a donor using the embodiment of the present invention illustrated in FIG. 3, at the outset, length adjustable sleeve 32 is in its fully extended state (i.e., not compressed or collapsed) and piercable member 34 is in a location proximally spaced from access site 23. During a collection procedure, a liquid or a sampling vial 20, as shown in FIGS. 2 through 5, may be inserted into the interior 42 of receptacle 40. As shown in FIGS. 2 and 3, vial 20, which is typically a vacuum sealed vial, may itself include a piercable cap 48. Such vials are available from the Beckon-Dickinson Co. of Franklin Lakes, N.J. and are sold under the trade name VACUTAINER®.

Referring first to FIG. 3, sampling vial 20 is inserted into the interior 42 of receptacle 40 so that cap 48 of vial 20 is pierced by the second piercing end 38 of piercing member 34, as shown in FIG. 4. Next, the entire vial with receptacle is moved forward by adjusting the length of sleeve 32. As shown, for example, in FIGS. 4 and 5, vial 20 with receptacle 40 is moved forward by compressing length adjustable sleeve 32. As length adjustable sleeve 32 is compressed, end 36 of piercing member 34 penetrates access site 23 as substantially shown in FIG. 4. Of course, as set forth above, any means for providing translational movement of piercing member 34 are within the scope of the present invention. In any event, continued translational movement of the vial and receptacle toward the access site 23 causes further penetration of the piercing member through the barrier and into the flow path 22 of the housing 18. Once a sufficient volume of blood has been collected, sampling vial 20 is removed and length adjustable sleeve 32 is returned or allowed to return to its original length. Of course, if additional samples are required, a new vial may be inserted into receptacle 40 and the process repeated. (During collection of the blood sample, it may be desirable to clamp off tubing 14 near container 16 and divert the blood as described above.) In any event, translational movement of the piercing member 34 through access site 23 and into flow path 22 allows a blood sample to be obtained directly from the flow path 22.

In addition, it will be recognized that the first end 36 of piercing member 34 is never exposed to the outside environment. This substantially reduces the risk that the piercing member and the blood in contact with piercing member 34 will be contaminated by foreign substances from outside of the housing, or that the technician will become injured due to an accidental "needle stick". Moreover, the apparatus of the present invention also provides a pre-assembled, integrated sampling system that includes the piercing member and the receptacle for receiving a sampling vial. Alignment of the piercing member with the access site is not required by the technician because the piercing member is already disposed within the housing and is in line with the access site. All that is required to be provided by the technician is the sampling vial. In short, the present invention reduces the number of external components required for obtaining a sample.

The present invention has been described in accordance with the preferred embodiments. However, it will be understood that minor variations to the embodiments shown herein may be made without departing from the present invention which is specifically set forth in the appended claims.

That which is claimed:

1. Apparatus for obtaining a liquid sample from a fluid flow path comprising:

a housing including an inlet, an outlet and a flow path therebetween;

said housing comprising an access site communicating with said flow path between said inlet and outlet, said housing carrying a piercing member at a location proximally spaced from said access site and a length adjustable sleeve proximally attached to said access site to allow for translational movement of said piercing member toward said access site, said piercing member comprising first and second opposed piercing ends.

2. The apparatus of claim 1 wherein said housing comprises a receptacle including an interior adapted for receiving a liquid sample vial.

3. The apparatus of claim 2 wherein said piercing member comprises first and second opposed piercing ends, wherein said second end is disposed within the interior of said receptacle.

4. The apparatus of claim 1 wherein said piercing member comprises first and second opposed piercing ends.

5. The apparatus of claim 1 wherein said piercing member comprises first and second opposed piercing ends wherein said first end is disposed within said length adjustable sleeve.

6. The apparatus of claim 1 wherein said access site comprises a septum adapted for repeated piercing.

7. The apparatus of claim 1 wherein said housing comprises at least one wall defining said flow path, said access site being substantially coplanar with said wall.

8. The apparatus of claim 1 wherein said length adjustable sleeve comprises a flexible compressible sleeve.

9. The apparatus of claim 1, comprising a receptacle proximally attached to said length adjustable sleeve, said receptacle including an interior adapted for receiving a liquid sample vial, wherein said piercing member first end is disposed within said sleeve and said piercing member second end is disposed within said receptacle interior.

10. The apparatus of claim 9, wherein said length adjustable sleeve comprises a flexible compressible sleeve.

11. A disposable tubing set for processing blood comprising:

means for withdrawing blood from a blood source;

a container for receiving said blood;

a flow path between said withdrawing means and said container, said flow path including a housing comprising an inlet, an outlet and an access site communicating with said flow path between said inlet and outlet, said housing carrying a piercing member at a location spaced from said access site and a length adjustable sleeve proximally attached to said access site to allow for translational movement of said piercing member toward said access site.

12. The disposable tubing set of claim 9, wherein said container includes a selected amount of anticoagulant.

13. The disposable tubing set of claim 11, comprising a receptacle proximally attached to said length adjustable sleeve, said receptacle including an interior adapted for receiving a liquid sample container.

14. The disposable tubing set of claim 13, wherein said piercing member comprises first and second piercing ends and said first end is disposed within said length adjustable sleeve.

15. The disposable tubing set of claim 13, wherein said piercing member comprises first and second opposed piercing ends, wherein said first end is disposed within said length adjustable sleeve and said second end is disposed within said receptacle interior.

16. The disposable tubing set of claim 15 comprising a sample receiving vial, said vial including a cap piercable by said second piercing member end.

17. The disposable tubing set of claim 11, wherein said piercing member comprises first and second opposed piercing ends.

18. The disposable tubing set of claim 11, wherein said access site comprises a septum adapted for repeated piercing.

19. The disposable tubing set of claim 11, wherein said housing comprises at least one wall defining said flow path, said access site being substantially co-planar with said wall.

20. The disposable tubing set of claim 11, wherein said length adjustable sleeve comprises a flexible compressible sleeve.

* * * * *